United States Patent [19]

Allain, Jr.

[11] 4,350,164
[45] Sep. 21, 1982

[54] PORTABLE, LIFE MONITOR, MEDICAL INSTRUMENT

[76] Inventor: Joseph L. Allain, Jr., 4932 Chantilly Dr., New Orleans, La. 70126

[21] Appl. No.: 156,056

[22] Filed: Jun. 3, 1980

[51] Int. Cl.³ .............................................. A61B 5/04
[52] U.S. Cl. .................................... 128/639; 128/696; 128/731
[58] Field of Search ............................... 128/639–641, 128/696, 710, 643, 700, 701, 731–734, 741, 800, 801, 902, 905, 642

[56] References Cited

U.S. PATENT DOCUMENTS

| | | | |
|---|---|---|---|
| 2,327,874 | 8/1943 | De Jong | 128/800 |
| 2,983,273 | 5/1961 | Howell | 128/643 |
| 3,085,577 | 4/1963 | Berman et al. | 128/641 |
| 3,491,750 | 1/1970 | King | 128/715 X |
| 3,533,397 | 10/1970 | Scher | 128/741 |
| 3,614,763 | 10/1971 | Yannuzzi | 128/630 |
| 3,776,228 | 12/1973 | Semler | 128/639 |
| 3,830,227 | 8/1974 | Green | 128/701 |
| 3,848,582 | 11/1974 | Milani et al. | 128/639 |
| 3,991,747 | 11/1976 | Stanley et al. | 128/902 |
| 4,033,356 | 7/1977 | Hara | 128/801 |

FOREIGN PATENT DOCUMENTS

| | | | |
|---|---|---|---|
| 250557 | 3/1966 | Austria | 128/639 |
| 565237 | of 1957 | Italy | 128/741 |

OTHER PUBLICATIONS

David et al., "A Low Cost Portable Ventricular . . . discriminator", Med. Inst., vol. 7, No. 4, Sep.-Oct. 1973, pp. 237-239.

Primary Examiner—Lee S. Cohen
Attorney, Agent, or Firm—C. Emmett Pugh and Associates, Ltd.

[57] ABSTRACT

A self-powered life monitor in a pocket-size, portable container including a casing with electrode probes mounted on the casing which are capable of piercing the skin to rest in subcutaneous tissue. The monitor further includes an amplifier electrically connected to the electrode probes and to a "life" indicator. The monitor is used by placing the electrode probes at different positions in an area of the human body where electrical potential is indicative of life activity, such as the areas of the heart or brain. The amplifiers enhance the difference between the electrical potentials measured by the probes, and the indicator indicates the existence and strength of the electrical potential and hence the presence or absence of life. For brain activity detection, a first embodiment (note particularly FIGS. 2 and 7) has supplemental, swing-out, pivoting electrodes, while a second embodiment (FIGS. 8 and 9) has supplemental, spring-out electrodes. Additionally a triangularly-shaped, extender electrode is used for heart activity detection (note FIGS. 1 and 4).

5 Claims, 9 Drawing Figures

U.S. Patent    Sep. 21, 1982    Sheet 1 of 4    4,350,164
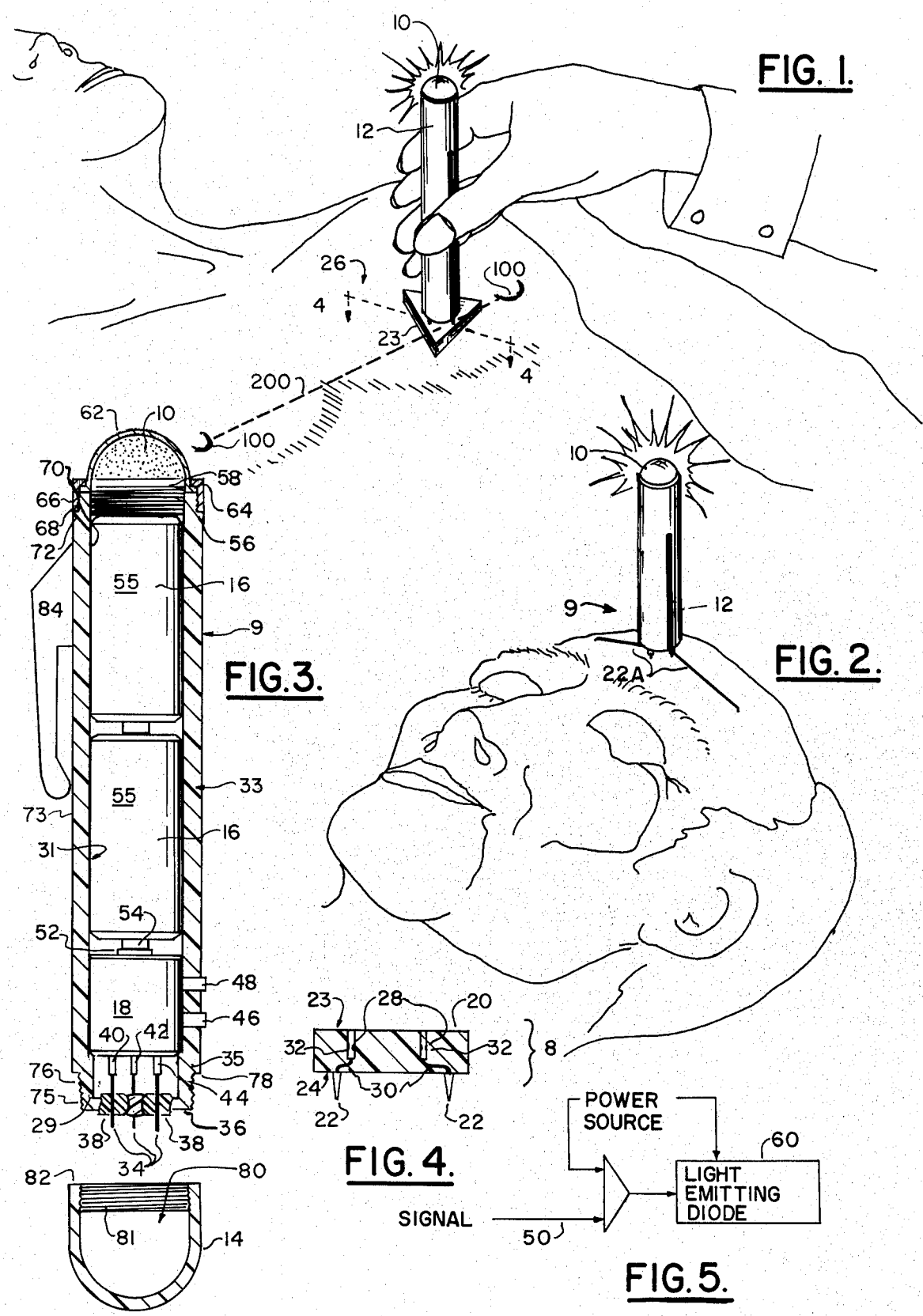

PORTABLE, LIFE MONITOR, MEDICAL INSTRUMENT

REFERENCE TO RELATED APPLICATIONS

This application is a substitute application of Ser. No. 810,925, now abandoned, filed June 29, 1977, entitled "Medical Instrument," which in turn was a substitute application of Ser. No. 308,231, now abandoned, filed Nov. 20, 1972, also entitled "Medical Instrument," the disclosures of which are incorporated herein by reference.

BACKGROUND OF THE INVENTION

1. Field of the Invention

The present invention relates to life monitoring systems, and the present invention has been found to be particularly useful in emergency procedures to determine life signs in apparent death situations, and hence will be discussed with particular reference thereto. However, the present invention is applicable to other life monitor, EKG and EEG detection situations as well.

2. Description of the Prior Art

The monitoring of voltage potential differences in the human body is well known in the prior art; see, for example, U.S. Pat. No. 3,706,308, issued Dec. 19, 1972, to John et al. Isolation of such signals is also well known in the art; see, for example, U.S. Pat. No. 3,699,389, issued Oct. 17, 1972, to Holsinger and U.S. Pat. No. 3,721,230, issued Mar. 20, 1973, to Ziernicki. It is also known to use the output of electrical signals to achieve light emitting devices, such as light emitting diodes of various sorts; see, for example, Van der Werde et al., "Medical and Biological Engineering," Vol. 6, No. 4, August 1960, pp. 447-448; and U.S. Pat. No. 2,516,882, issued Aug. 1, 1950, to L. Kalom.

Additionally, it is known to apply electrical signals to the human body for nerve and other responses; see, for example, U.S. Pat. No. 2,298,506, issued Oct. 13, 1942, to Parker; U.S. Pat. No. 3,664,329, issued May 23, 1972, to Naylor. Also, the remote, electronic monitoring of body functions through subcutaneously implanted electronic devices is known; see, for example, U.S. Pat. No. 3,209,081, issued Sept. 28, 1965, to Ducote et al., and U.S. Pat. No. 3,212,496, issued Oct. 19, 1965, to Preston.

Other references considered pertinent to the invention in applicant's prior application Ser. No. 810,925, are set out below:

| Patent Number | Inventor(s) | Issue Date |
|---|---|---|
| -U.S. Patents- | | |
| 3,491,750 | B. B. King | Jan. 27, 1970 |
| 3,776,228 | H. J. Semler | Dec. 4, 1973 |
| 4,033,356 | T. Hara | July 5, 1977 |
| 3,085,577 | R. M. Berman et al | Apr. 16, 1963 |
| 2,983,272 | W. L. Howell | May 9, 1961 |
| 3,533,397 | J. M. Scher | Oct. 13, 1970 |
| 3,614,763 | A. Yannuzzi | Oct. 19, 1971 |
| 3,848,582 | D. L. Milani | Nov. 19, 1974 |
| 2,327,874 | H. De Jong | Aug. 24, 1943 |
| 3,830,227 | H. L. Green | Aug. 20, 1974 |
| 3,991,747 | A. L. Stanly et al | Nov. 16, 1976 |
| -Foreign Patents- | | |
| ITALIAN "Brevetto": 565,237 | | May 5, 1955 |
| AUSTRIAN PATENT: 250,557 | | Nov. 25, 1966 |
| -continued | | |
| Patent Number | Inventor(s) | Issue Date |
| -Publication- | | |
| MEDICAL INSTRUMENTATION Vol. 7, No. 4, pp. 237-238 (article entitled "A low-cost, portable ventricular fibrillation-cardiac arrest discriminator" by David, et al). | | |

However, none of this prior art teaches a portable, pocket-size, self-contained and self-powered life monitor system capable of use under emergency situations to determine voltage potential differences indicative of the existence of life in, for example, apparent death situations adaptable for testing either or both the brain and/or heart functions.

GENERAL DISCUSSION OF THE INVENTION

The present invention uses a very simple but highly effective design of a compact, portable, pocket-size monitor to indicate life indicating voltage potential differences at different, spaced points of the human body, particularly in the heart and brain areas of the human body. The monitor includes a voltage potential difference detection and amplification system with high noise immunity. The monitor also includes an indicator connected to the amplification system that displays the existence and strength of such voltage potential differences. The monitor is packaged so that it is portable and pocket-size and includes an internal power supply.

For brain activity detection requiring a relatively large electrode spacing, a first embodiment (note particularly FIGS. 2 and 7) has supplemental, fold down, swing-out, pivoting electrodes, while a second embodiment (FIGS. 8 and 9) has supplemental, spring-out electrodes. Additionally, a triangularly-shaped, extender electrode is used for heart activity detection (not FIGS. 1 and 4).

BRIEF DESCRIPTION OF THE DRAWINGS

For a further understanding of the nature and objects of the present invention, reference should be had to the following detailed description, taken in conjunction with the accompanying drawings, in which like parts are given like reference numerals and wherein:

FIG. 1 is a perspective view of the preferred embodiment of the medical instrument of the present invention showing the detection of voltage potential differences in the area of the heart using a unitary set of extender electrodes;

FIG. 2 is a perspective view of the preferred embodiment of the medical instrument of the present invention showing the detection of voltage potential differences in the area of the brain using supplemental, fold-down, greatly spaced electrodes;

FIG. 3 is a side view of the basic body of the preferred embodiment of the medical instrument of the present invention, partly in cross-section and partly in elevation;

FIG. 4 is a partial, side, cross-sectional view of another portion of the preferred embodiment of the medical instrument of the present invention taken along section lines 4—4 of FIG. 1;

FIG. 5 is a simplified electrical block diagram of the electronics of the preferred embodiment of the medical instrument of the present invention;

FIG. 6 is a detailed electrical schematic of an alternate embodiment of the electronics for the preferred embodiment of the medical instrument of the present invention; while

FIG. 8 is a side view (similar in perspective to FIG. 3) of the basic body of a second, alternate embodiment of the medical instrument of the present invention, partly in cross-section and partly in elevation, with its supplemental, spring-out electrodes held in; while

BRIEF DESCRIPTION OF THE PREFERRED EMBODIMENTS

Introduction

Figure 6:
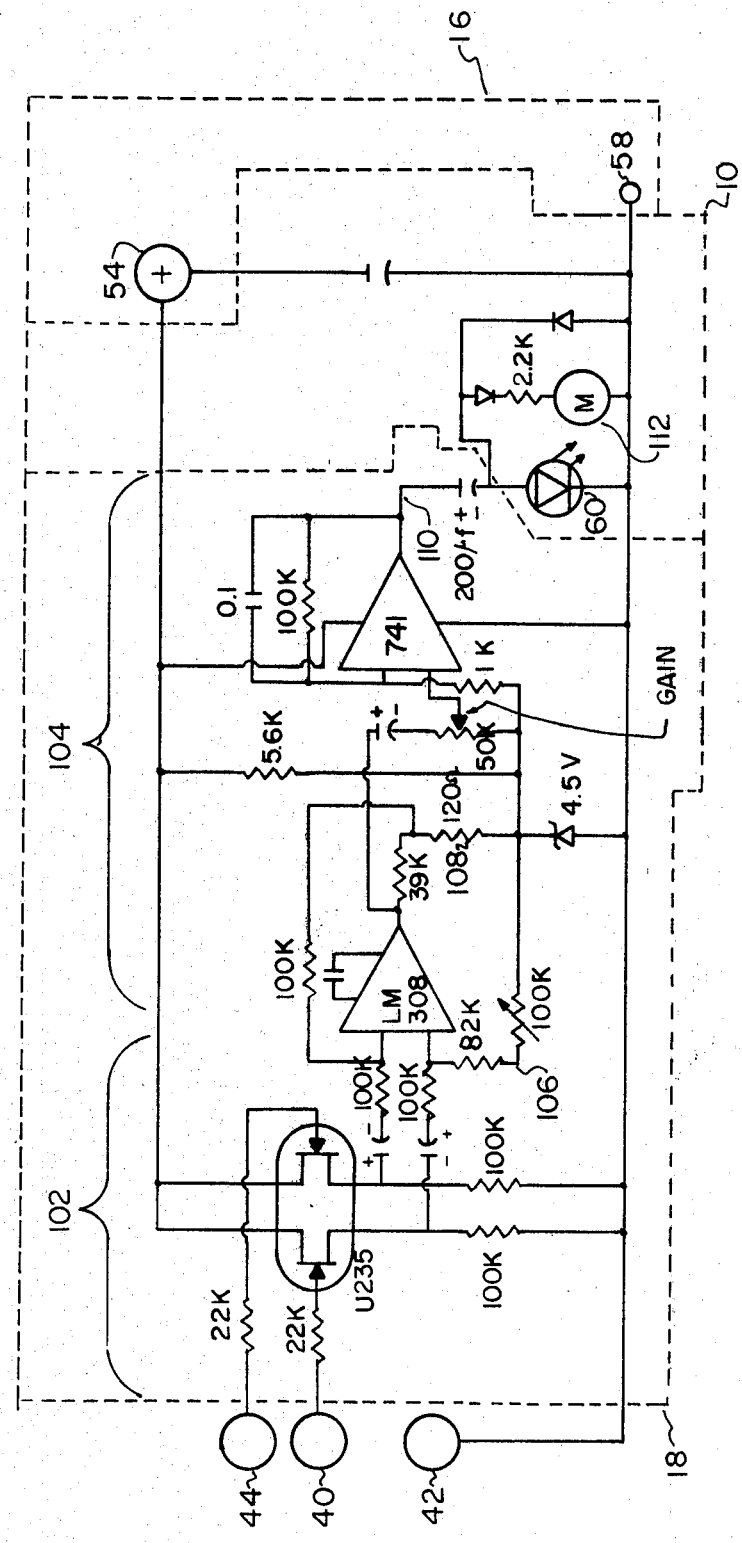

A human being is officially dead when the doctor pronounces him dead. The doctor bases this pronouncement upon clinical observations. With the advent of modern technology, it is now possible to revive an individual who might previously have been pronounced dead. The embodiments of the life monitor medical instrument of the present invention may be used to assist the operator thereof to distinguish between clinical death and actual death of a human being. The life monitor is portable, pocket-size and self powered. It enables the operator to determine voltage potential differences indicative of the existence of life in, for example, clinical death situations prior to the commitment of the scarce resources needed to revive an individual. Such a device is desirable because it gives instantaneous data relevant to the presence or absence of electrical activity of, for example, the heart (showing anything from ventricular fibrillation to normal heart beat, thereby distinguishing from cardiac standstill) or the brain. This information would assist clinicians to establish a diagnosis of life or death and assist in determining when to start or not start resuscitative efforts, and to help determine when such efforts should be abandoned.

A first embodiment (FIGS. 1-3) in which supplemental, greatly spaced electrodes are provided in a swing or fold down version will initially be described in detail, and then a second, similar embodiment (FIGS. 8 and 9) will be described in which the supplemental electrodes are provided in a spring out version. In both embodiments a triangularly-shaped, supplemental electrode extender (FIGS. 1 and 4) can be used, particularly in the heart area (FIG. 1). The supplemental, greatly spaced, laterally moveable electrodes are particularly useful in the brain area, as for example is shown for the first embodiment in FIG. 2.

First Embodiment and Its Method of Use

As shown in FIGS. 1-4, the first preferred embodiment of the life monitor of the present invention comprises electrode extender element 8, detector 9, indicator 10 and supplemental, greatly spaced fold-down electrodes 22A.

FIG. 5 shows a block diagram of the electrical circuit used in the preferred embodiment of the present invention, comprising an amplifier 6, having an input 50 and connected to light emitting diode 60.

Electrode extender element or system 8 includes a triangularly-shaped body 20 having upper end 23 and lower end 24. The body may be made of metal or glass or other material capable of being sterilized. Electrodes 22 extend from the lower end 24 a distance sufficient to permit insertion of the needle electrodes 22 through the epidermal layer 26 (if desired) of skin to the subcutaneous tissue below (not shown). The electrodes 22 are approximately three-eighths inch in diameter and are physically separated from each other by a desirable distance as will be more fully discussed hereinafter. The upper end 23 includes female receptacles 28. Resilient clips 32 may be located in female receptacles 28. The female receptacles 28 are electrically connected to needle electrodes 22 by electrical connectors 30. Electrical connectors 30 are usually molded into body 20.

Detector 9 includes container 12, end cap 14, power supply 16 and detector/amplifier 18. Container 12 includes casing 33 with bore 29 and enlarged bore 31 through it, forming shoulder 35 at the end of enlarged bore 31. The lower end of detector/amplifier 18 rests against shoulder 35. Electrode connectors 34 extend from the bottom end 36 of casing 33. Connectors 34 are resiliently mounted to the bottom end 36 by resilient seals 38. Connectors 34 have a diameter substantially equal to the diameter of female receptacles 28. The length of connectors 34 below bottom end 36 is slightly greater than the length of female receptacles 28 from the upper end 23 of body 20 to the resilient clip 32.

The upper end of connectors 34 are connected by screw connection or solder or other suitable connection means to terminals 41, 42, 44. Terminals 40, 42, 44 are electrically isolated from each other and electrically connected to detector/amplifier 18. The signals from connectors 40, 42, 44 form signal line 50 of FIG. 5.

Switches 46 and 48 are resiliently mounted on casing 33 and mechanically interlocked to switches (not shown) in detector/amplifier 18 by means well known in the art. The switch of detector/amplifier 18 connected to switch 46 changes the gain of the amplifier section (not shown) of detector/amplifier 18 by resistor switching or other means well known in the art. The switch of detector/amplifier 18 connected to switch 48 shunts a reference power source in place of the potential voltage drop between terminals 40, 44 by means well known in the art, such as switching a terminal to voltages impressed across resistors.

Detector/amplifier 18 connects by electrically conductive terminal 52 to one electrically conductive end 54 of batteries 55 forming power supply 16. For example, a standard nine volt transistor battery capable of delivering twelve milliamps when indicator 10 is on and three milliamps when indicator 10 is off may be used.

The other conductive end of power supply 16 abuts one end of electrically conductive spring 56 of indicator 10 as is well known in the art. The other end of the spring 56 forms terminal 58. Terminal 58 is electrically connected (not shown) to indicator 10. A terminal strip (not shown) from detection/amplifier system 18 is also connected to indicator 10.

Indicator 10 includes a light source, such as a light emitting diode 60 (FIG. 5) made of gallium arsenide, marcellized gallium or the like, which emits visible light upon the application of voltage, the intensity of light increasing with increasing magnitude of the applied voltage. Indicator 10 also includes lens 62 covering and protecting light emitting diode 60. Lens 62 includes shoulder 64. Indicator 10 further includes lens holder 66 having a threaded bore 68, the outer diameter of the bore 68 being substantially equal to the diameter of the lens shoulder 64.

The upper end 70 of casing 33 has threads 72 of the same pitch as threaded bore 68 and is narrower than the main body portion 73 of casing 33. Substantially horizontal shoulder 74 is formed between upper end 70 and main body portion 73. Upper end 70 also includes uppermost shoulder 71. Shoulder 74 is juxtaposed to the lowest end of lens holder 66.

The lower end 75 of casing 33 has threads 76 and is narrower than the main body portion 73 of casing 33. Substantially horizontal shoulder 78 is formed between lower end 75 and main body portion 73.

Cap 14 includes internal bore 80 having threads 81 and upper flat end 82. Threads 81 are the same pitch as threads 76, and the depth of thread 81 is slightly greater than the thread length of threads 76. The depth of bore 80 below threads 81 is greater than the length of electrode connectors 34 below shoulder 36.

Clip 84, for attaching the monitor instrument to for example a shirt pocket, is attached to the upper portion of casing 33. The compact size of the monitor instrument allows for its convenient carrying in such a pocket.

Detector 9 is assembled by first attaching electrodes 34 to terminals 40, 42, 22 (the device can be pre-assembled). Detector/amplifier 18 is then inserted into casing 33 and the switches (not shown) of detector/amplifier 18 is aligned with switches 46, 48. Switches 46, 48 also hold detector/amplifier 18 against shoulder 35. Electrodes 34 are then sealed to bottom end 36 by resilient seals 38. Batteries 55 are then inserted through bore 31 until end 54 abuts conductive terminal 52. Indicator 10 is then placed on uppermost shoulder 71 and lens holder 66 is screwed onto threads 72 until shoulder 64 is tightly held in place. Cap 14 is then placed on lower end 75 until shoulders 78, 82 abut. Detector 9 is normally clipped to a coat pocket by clip 84. Electrode system 8 is separately and sterily packaged for use.

In use, cap 14 is removed from detector 9. Electrodes 34 are then firmly inserted into female receptacles 28 and held in place by resilient clips 32. Switch 48 is then depressed to check the operation of detector 9. If the heart potential is to be checked first, switch 46 is set to modify the amplification of detector/amplifier 18. Optimally, the area of placement of electrodes 22 should be cleaned with alcohol or other sterile cleaning agent. Needle electrodes 22 are then placed onto, or inserted through, the epidermal layer 26 of skin to the subcutaneous tissue below (not shown). The needle electrodes 22 corresponding to the terminals 40, 44 should be placed approximately in the same horizontal line as the breast nipples 100. Placement should be on the inside of the nipples, (i.e., toward the center of the body as is indicated by dotted line 200) and optimally midway between the two nipples 100. Indicator 10 is then monitored to determine any life signs.

Figure 7:
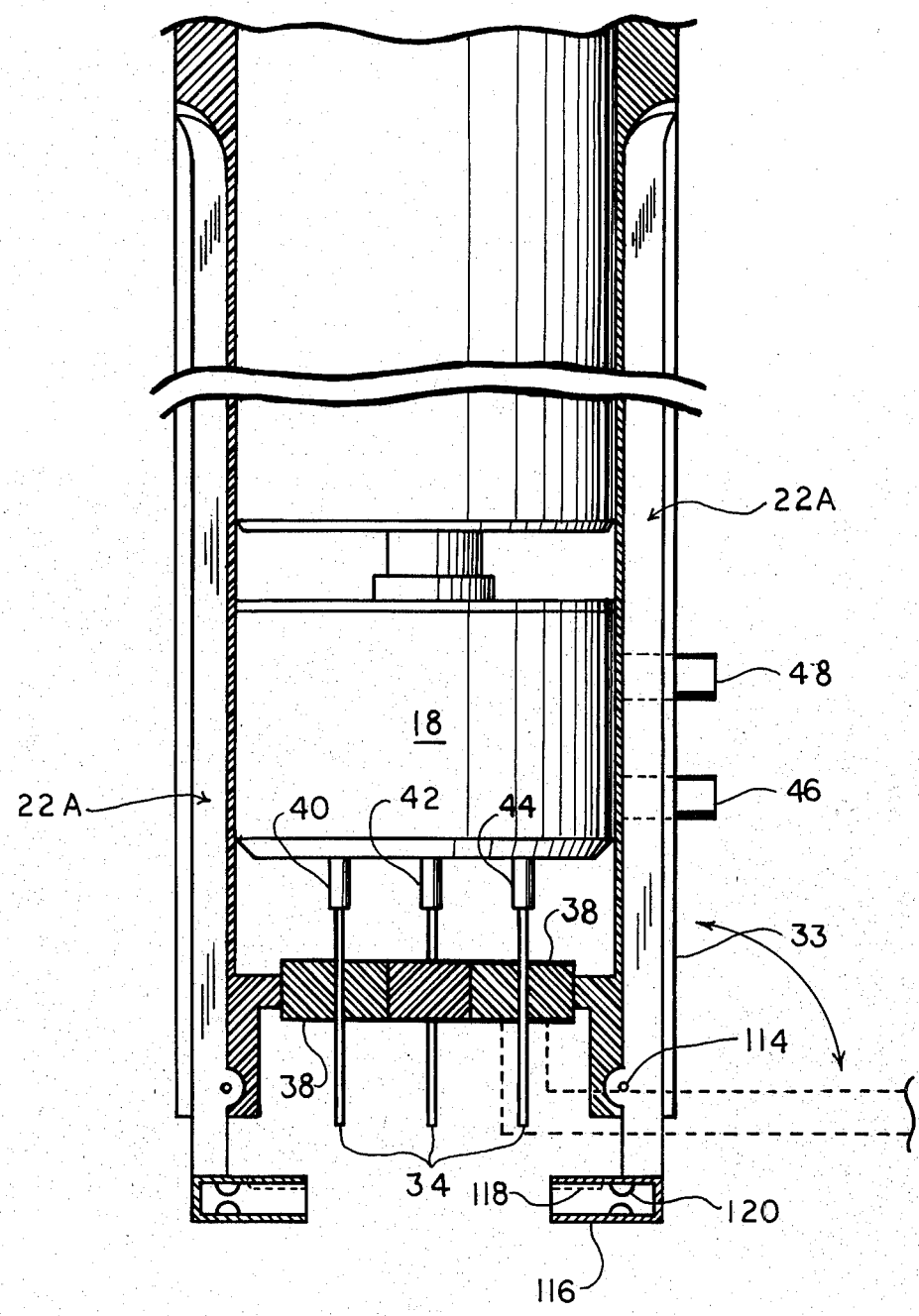
FIG. 7 is a partial, side, close-up view of the bottom portion of the preferred embodiment, showing in phantom-line the interconnection of one of the supplemental fold-down electrode with an internal electrode of the basic body of the device.

As shown in FIG. 2, similar operations occur for detection of voltage potential differences of the brain. However, the greater distance between electrodes 22 would be required. In detection of voltage potential differences of the brain, an exemplary distance of ten centimeters (10 cm.) should be provided. Thus, as is illustrated in FIG. 2, fold down electrodes 22A could be provided to give the desired ten centimeters (10 cm.) distance. In FIG. 2, long electrodes 22A are shown in their extended position. Each of the fold-down electrodes may be pivotably mounted by hinges or other mechanism (see for example FIG. 2) to casing 33. Casing 33 includes grooves (FIG. 2) cut or molded therein to receive the fold-down electrodes 22A in their retracted position parallel to casing 33. Each electrode 22A includes an electrode tip, an insulating body with a conductor through the center, and a female receptacle. The conductor is connected mechanically and electrically to the tip at one end of its ends. The female receptacle 16 is similar in structure to female receptacle 28, and the conductor is connected mechanically and electrically to the receptacle at the other of its ends. With the electrodes 22A pivotably mounted to casing 33, the receptacles are spaced from the hinges a sufficient distance such that the receptacles pivot to a position to telescopically receive connectors 34 when the electrodes are in their extended position substantially perpendicular to casing 33. FIG. 7 shows a partial, side, cross-sectional view of the lower end of detector 9 showing exemplary details of the mount for electrodes 22A. As can be seen, electrodes 22A are each pivotably mounted by a pin 114 and have disposed at the lower end thereof a female receptacle 116. Receptacles 116 have cut-off portions 118 on the top thereof to receive connectors 34, and resilient clips 120 to insure a snug electrical and mechanical fit between connectors 34 and receptacle 116.

Human skin is resilient and therefore the uneven vertical spacing of connectors 34 caused by the receptacles covering two of the connectors 34 should not prevent good electrical contact of the uncovered connector 34 with the skin. However, should the vertical unevenness of the conductors hamper good electrical conductivity of the tips and the uncovered connector 34, an extender (note FIG. 7) comprising a vertically juxtaposed female receptacle and tip may be placed over the uncovered connector 34 to even the vertical spacing of the connectors from the skin. Alternatively, such electrodes 22A could be larger and separately provided in a separate sterile package for connection with connectors 34 for use and discarded after use.

After the patient is monitored, electrode system 8 is detached and resterilized. Cap 14 is then replaced onto detector 9 and the monitor placed back into for example the user's pocket.

Alternate Electronics

If electrodes 22 are not inserted into the skin, background electrical signals (noise) may be introduced into the detector/amplifier 18. For electrodes not inserted into the skin, special signal conditioning may be necessary, and such alternate electronics are schematically illustrated in detail in FIG. 6. As shown in FIG. 6, the signals from terminals 40, 44 are first preamplified by preamplifier section 102. The difference of the amplified signals is then sent through filter/amplifier section 104 to filter common and normal mode signals, especially 60 cycle noise. Filter/amplifier section 104 also contains null and gain adjustments 106, 108, respectively. The output 110 of filter/amplifier 104 is fed to indicator 10, including light emitting diode 60 and meter 112. Common terminal 42 is connected to the common terminal 58 of power supply 16.

The gain 108 sets the sensitivity of detector 9.

The null adjustment 106 sets the ideal common mode rejection point. Adjustment of this setting will null out unwanted artifacts such as 60 cycle noise. The adjustment is rather coarse and in some instances will not have to be touched but should be left at the approximate center of the adjustment range. Alternatively an internal computer chip could be provided to make the null adjustment automatically.

In using the detector 9 without insertion of electrodes into the skin, it is of the utmost importance that the body be clean. Furthermore, electrode paste, gel, or alcohol pads should be placed underneath the electrodes (one under each electrode).

After the alcohol pads are in place underneath the electrodes and the electrodes are solidly mated to the subject's chest, the gain 108 may be then increased slowly until the meter 112 shows the EKG beat and the LED light 60 flashes at the EKG rate. Again alternatively an internal computer chip could be provided to make the gain adjustment automatically. If the meter 112 or the light 60 vascillates or flashes erratically, the null adjustment 106 may be varied to find the best operating point. If the null adjustment 106 fails to bring in clean data, one may suspect that the electrodes are improperly placed or contaminated. It is important to increase gain slowly and break off when too much gain is used.

Second Embodiment

Figure 9:
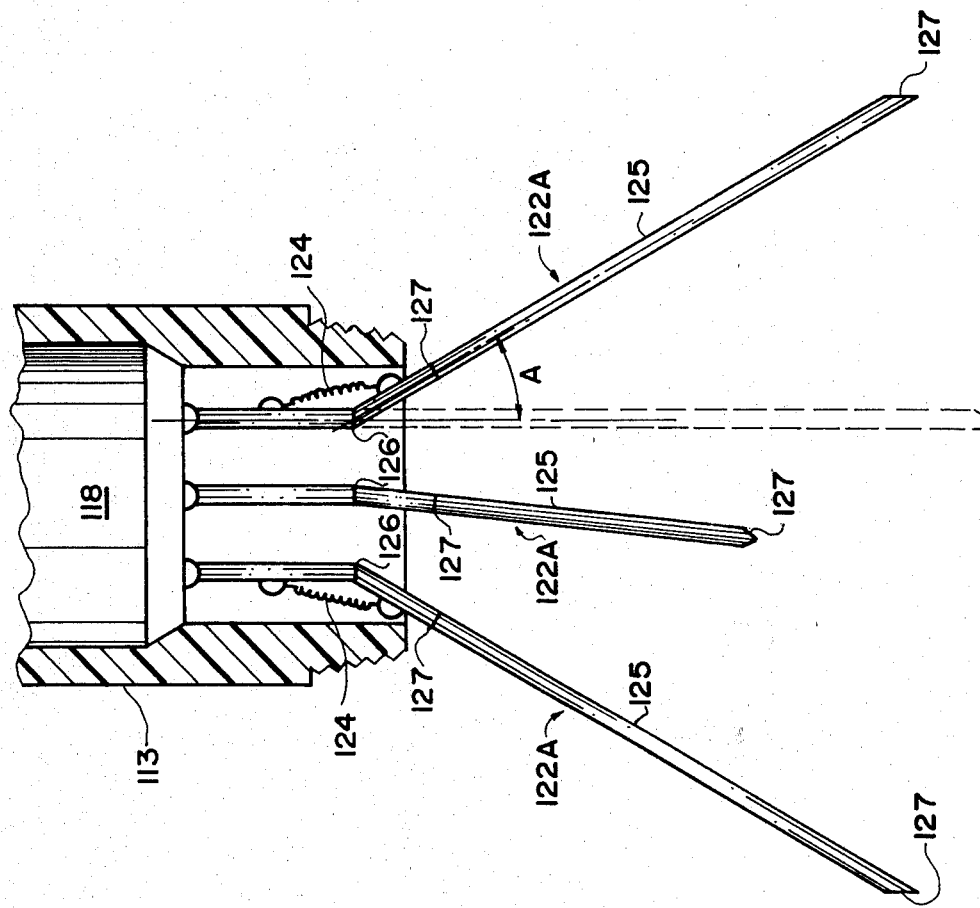
FIG. 9 is a side, partial view of the alternate embodiment similar to FIG. 8 but with the cap completely removed and the supplemental electrodes sprung out for brain use.
Figure 8:
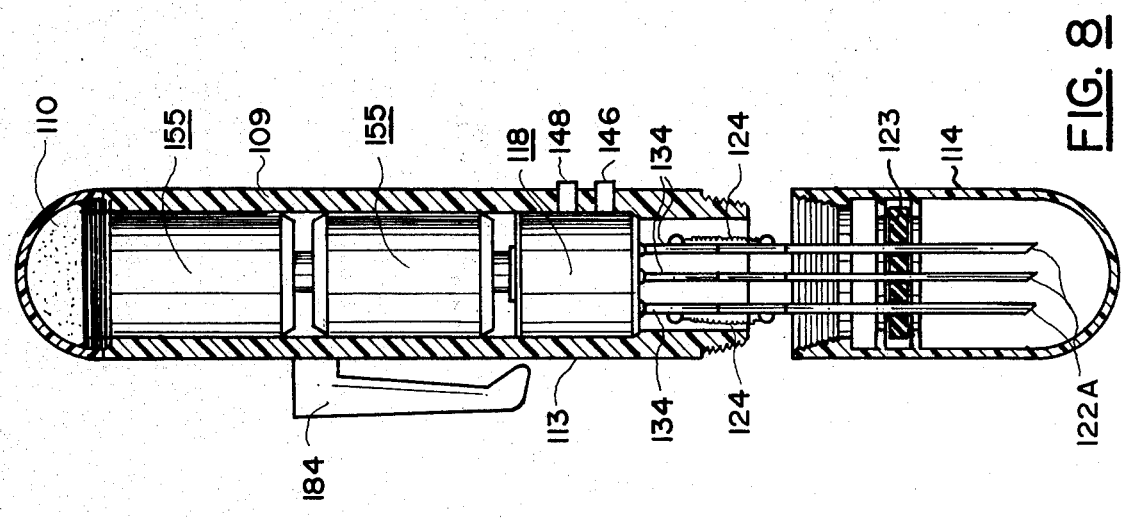

As can be seen in FIGS. 8 and 9, a second, alternative embodiment, similar to the first embodiment of FIGS. 1 and 3, is provided as an exemplary variation having supplemental spring-out electrodes 122A in place of the fold-down electrodes 22A. Because the two embodiments are otherwise substantially identical and for the sake of brevity, a detailed description of the similar elements will not be provided except to note that the analogous elements of the second embodiment are numbered similarly to that of the comparable elements of the first embodiment but in a hundred series.

FIG. 8 shows the alternate monitor with its supplemental electrodes 122A in their storage or close-in disposition held in that position by insulated holder 123. When it is desired to laterally extend the electrodes 122A into their relatively greatly spaced disposition, the holder 123 is slid down and off the ends of the electrodes 122A, allowing them to spring out an angle "A" of for example thirty degrees under the action of resilient spring biases or connectors 124.

It is noted that the lower portions 125 of the electrodes 122A are pivotedly joined to the electrode connector portions 134 to allow pivoting from the vertical disposition of FIG. 8 to the sprung out, angled and spaced disposition of FIG. 9 with stop lock joints 126 preventing their further movement pass the desired spacing and maintaining them in their spaced, angled disposition during use to check for example for any brain activity. After use, sufficient force is applied inwardly against the lower portions 125 of the electrodes 122A to overcome the locking force of the joints 126, and the electrodes 122A are then moved into their vertical dispositions and the holder 123 slid up and on them holding them in position for storage or use as close-in electrodes for example for the heart area.

It is noted that the lower portion 125 of the electrode 122A includes a telescoping slip joint 127 allowing for ease of removal and replacement of the terminal end portion of the electrode 122A. It is also noted that the holder 123 is held within the cap 114 but allowed to rotate within it as the cap is threaded on and off the end of the casing 113. Alternatively the holder 123 could be provided as a totally separate item.

Exemplary dimensions for the spring loaded electrodes 122A are for example two-and-a-half inches in length from the tip 127 to the joint 126 and a half inch in length for the connector section 134.

Additionally, if desired, the supplemental electrode extender element 22 (modified in size as needed) of FIGS. 1 and 4 can be used with this embodiment by merely slipping it on the terminal ends of the electrodes 122A when in their vertical dispositions.

Conclusion

Thus, there has been disclosed two exemplary embodiments of the life monitor medical instrument of the present invention, both of which can be used to monitor any life activity at either or both the heart and/or brain areas.

Although the systems and embodiments described in detail supra have been found to be satisfactory and preferred, many variations in structure and method are possible. For example, electrode system 8 may be made of any material and discarded after use. Also, electrodes 22 may be made removable from electrode system 8, and only electrodes 22 discarded. Moreover, electrode system 8 and detector 9 may be electrically coupled by wire without physical engagement of electrodes 34 into female receptacles 28.

The above are of course only exemplary of the many possible changes or variations.

Because many varying and different embodiments may be made within the scope of the inventive concept herein taught and because many modifications may be made in the embodiments herein detailed in accordance with the descriptive requirements of the law, it should be understood that the details herein are to be interpreted as illustrative and not in a limiting sense.

What is claimed is:

1. A portable life monitor for use in monitoring body tissue for electrical signals, comprising:

electrode detector means for detecting such electrical signals in such tissue including electrode means having a first set of electrodes for electrically connecting said electrode detector means to such tissue;

a first body having amplifier means for amplifying such electrical signals and indicator means for receiving and displaying said amplified electrical signals;

first connection means for detachably electrically connecting said amplifier means to said electrode detector means;

a second, separate set of electrodes; and fold down means connected to said second set of electrodes for mechanically supporting said second set of electrodes on said first body in two positions, a first position being substantially parallel to said first body and a second position being substantially perpendicular to said first body; and wherein said first connection means detachably electrically connects said second set of electrodes to said amplifier means in said second position.

2. The monitor of claim 1 wherein said first body includes clip means for holding said body to articles of clothing.

3. The monitor of claim 1 wherein said first body further includes gain change means for changing the gain of said amplifier means.

4. The monitor of claim 1 wherein said first body further includes:

power means within said body for supplying power for said amplifier means and said indicator means; and power testing means for testing the ability of said power means to supply said power using said indicator means.

5. An electrical potential measuring apparatus for use in detecting voltage difference between different places in the human body, comprising:

a body;

electrical conductors mechanically supported by said body;

at least two electrodes, each electrode including pivot means for pivotably mounting said electrode on said body and conductor means for detachably electrically connecting said electrode to one of said electrical conductors in one position of said electrode for transmission of the voltage differences to said one of said electrical conductors;

indicating means for indicating the presence of the voltage differences, said indicating means being electrically connected to said electrical conductors; and extension means, including an electrode, said extension means being mechanically and electrically connected to one of said conductors, for spacing all conductors substantially equidistant from the human body when said electrodes are in said one position.

* * * * *